US006558734B2

(12) United States Patent
Koulik et al.

(10) Patent No.: US 6,558,734 B2
(45) Date of Patent: May 6, 2003

(54) METHODS FOR MODIFYING SURFACES OF ARTICLES

(75) Inventors: Edouard Koulik, Golden Valley, MN (US); Cahalan T. Patrick, Nashua, NH (US); Hiroo Iwata, Osaka (JP)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/779,535

(22) Filed: Feb. 9, 2001

(65) Prior Publication Data

US 2002/0150671 A1 Oct. 17, 2002

(51) Int. Cl.[7] .................................................. B05D 3/02
(52) U.S. Cl. ........................ 427/2.24; 427/2.3; 427/379; 427/393.5; 427/412.1
(58) Field of Search ................................. 427/2.24, 2.3, 427/412.1, 379, 393.5

(56) References Cited

U.S. PATENT DOCUMENTS

| | | | |
|---|---|---|---|
| 4,822,741 A | | 4/1989 | Banes |
| 5,229,172 A | * | 7/1993 | Cahalan et al. .............. 427/536 |
| 5,494,756 A | * | 2/1996 | Siegel ....................... 427/2.11 |
| 5,607,475 A | | 3/1997 | Cahalan et al. |
| 5,782,908 A | * | 7/1998 | Cahalan et al. ............. 427/2.24 |
| 5,843,149 A | * | 12/1998 | Ebert et al. ................. 128/899 |
| 6,024,918 A | * | 2/2000 | Hendriks et al. .............. 422/44 |
| 6,117,979 A | | 9/2000 | Hendriks et al. |
| 6,303,179 B1 | * | 10/2000 | Koulik et al. ............... 427/2.26 |

FOREIGN PATENT DOCUMENTS

| | | | |
|---|---|---|---|
| JP | 05-192393 | * | 8/1993 |
| JP | 07-192494 | * | 7/1994 |
| WO | WO 98/08551 | * | 3/1998 |
| WO | WO 00/71612 | * | 11/2000 |

OTHER PUBLICATIONS

Nelson et al, ASAIO J., 39(3), MM310–M313, 1993.*
Petraitis, Book of Abstracts, 216th ACS National Meeting, Boston, Aug. 23–27, PMSE–276, 1998.*
Khorasani et al, Radiat. Phys. Chem. 55(5–6), pp 685–689, 1999.*
W. Iwata et al., "Surface Graft Polymerization onto Silicone", *J. Applied Polymer Science*, 49 1041–46 (1993).
Rubber Fabrication: Silastic Silicone Rubber, Dow Corning (Midland, MI), Copyright 2000, http://www.dowcorning.com/page_generate.pl?idx9250 (printed Sep. 5,2000).

* cited by examiner

*Primary Examiner*—Erma Cameron
(74) *Attorney, Agent, or Firm*—Thomas F. Woods; Eric R. Waldkoetter; Tom G. Berry

(57) ABSTRACT

This invention relates to methods for preparing articles having modified surfaces. Preferably the articles are medical devices. Preferably the surfaces are elastomeric. Preferably the articles having modified surfaces are useful for immobilizing biologically active agents on the surfaces.

7 Claims, No Drawings

METHODS FOR MODIFYING SURFACES OF ARTICLES

FIELD OF THE INVENTION

The present invention relates to methods for modifying surfaces of articles.

BACKGROUND

Silicones are widely used in the medical industry. A variety of products are made from silicones including implantable leads, catheters, sensors, and shunts. The wide usage of silicones is due to the variable mechanical properties, the ease of manufacture, the low rate of degradation, and high oxygen transfer. However, silicones lack a number of surface related properties that are desirable in the medical device industry, such as lubricity, hydrophilicity, and blood compatibility.

A variety of approaches have been undertaken in attempts to modify the surface properties of silicones to make them more attractive substrates for the medical device industry. However, the success of the various approaches has been limited by the inherent hydrophobicity and inertness of the silicone surface. Approaches that have been used in attempts to activate the surface include flame treatment, acid treatment, and corona discharge treatment. The utility of these approaches has been limited by a variety of problems including, for example, the use of corrosive chemicals and/or the necessity of oxygen exclusion. In addition, some of the approaches require that the low molecular weight silicones that are present in commercial silicones be extracted before the surface treatment is carried out.

A need exists in the medical device industry for a simple and effective method of modifying the surface of silicones to provide desirable surface properties.

A few reports of surface modification have appeared in the art, some examples of which may be found in the patents and publications listed in Table 1 below.

TABLE 1

Patents and Publications

| U.S. Pat./Publication No. | Inventor(s) | Issue/Publication Date |
| --- | --- | --- |
| U.S. Pat. No. 5,607,475 | Cahalan et al. | 4 March 1997 |
| U.S. Pat. No. 4,822,741 | Banes | 18 April 1989 |

Technical Publications

Iwata et al., *J. Applied Polymer Science*, 49:1041–46 (1993). Rubber Fabrication: Silastic Silicone Rubber, Dow Corning (Midland, Mich.), Copyright 2000.

All patents and publications listed in Table 1 above are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the patents and publications of Table 1 may be modified advantageously by using the teachings of the present invention.

SUMMARY OF THE INVENTION

The present invention has certain objects. That is, various embodiments of the present invention provide solutions to one or more problems existing in the prior art with respect to methods for preparing articles having modified silicone surfaces. Those problems include methods that require the use of corrosive chemicals, methods that require oxygen exclusion, methods that require the extraction of low molecular weight silicones, and methods that lead to poor surface properties (e.g., adhesion and uniformity) due to factors including, for example, the presence of unextracted low molecular weight silicones in the article and the inert chemical nature of the silicone itself. Various embodiments of the present invention have the object of solving at least one of the foregoing problems. While some methods were capable of solving at least some of the foregoing problems, they were generally not employed because of their prohibitively high cost or difficult manufacturing processes. It is therefore another object of the present invention to provide an improved method that may allow the surface-modified articles to be economically manufactured and sold at low cost, yet still fulfill at least one of the foregoing objects.

In comparison to known methods for preparing articles having silicone surfaces, various embodiments of the present invention may provide one or more of the following advantages. The present invention may provide articles having modified silicone surfaces with improved properties over articles with silicone surfaces known in the art. For example, surface-modified articles of the present invention are preferably biocompatible. Biocompatibility may be important in preventing complications such as adverse reactions by the body when the article is inserted in human or animal tissue.

The present invention also provides advantageous methods for preparing articles having modified silicone surfaces. Methods of the present invention allow for surface modification of such articles without the need for extracting low molecular weight silicones. Such methods may provide economic advantages as well as product quality improvements. For example, methods of the present invention preferably may be carried out by simple, rapid procedures without the need for expensive equipment.

Definitions

As used herein, "silicone" refers to a polysiloxane. Preferably silicones are poly(diorganosiloxanes). Preferably silicones are elastomeric.

As used herein, "elastomeric" refers to substances having the properties of natural, reclaimed, vulcanized, or synthetic rubber, in that they stretch under tension, have a high tensile strength, retract rapidly, and recover to about their original dimensions. Preferably elastomers have a tensile strength of at least about 2 megapascals (MPa) (290 pounds per square inch, psi) and more preferably at least about 4 MPa (580 psi). Preferably elastomers have an elongation at break of at least about 50% and more preferably at least about 100%.

As used herein, "surface-modified" refers to material that is chemically or physically altered in a surface layer compared to the material in the layer below the surface layer. Preferably the surface-modified layer is at least about 1 micrometer thick and at most about 100 micrometers thick.

An "amide-functional surface" refers to a material having at least amide-functional groups on the surface. An "amine-functional surface" refers to a material having at least amine-functional groups on the surface. The surface can also include other functional groups. Surfaces having such functional groups (amide groups, amine groups, etc.) are referred to herein as "functionalized" surfaces. Preferably the functionalized surface includes a polymer and more preferably a hydrogel polymer. Generally, a hydrogel polymer is distinct from a solid polymeric material in the amount of water contained therein. Typically, a solid polymeric material includes less than about 10% by weight water.

As used herein, the term "curing" includes hardening, crosslinking, polymerizing, chain extending, and other related chemical reactions. Preferably a cured material has undergone sufficient hardening, crosslinking, polymerizing, or chain extending to provide a material in the solid state.

As used herein, "partially-cured" means that peroxide remains that has not decomposed during the curing reaction.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood or other devices that contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like, which are placed into the blood vessels or the heart for purposes of monitoring or repair.

As used herein, "biologically active agent" means a substance that has an effect on living tissue. Biologically active agents include, for example, therapeutic agents, which are substances that tend to prevent and/or overcome disease and/or promote recovery. As such, biologically active agents also include, for example, biologically active molecules (biomolecules) such as drugs.

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection), inflammatory reaction, or blood clotting, for example.

DETAILED DESCRIPTION OF THE PREFERRED EMBODIMENTS

In one aspect, the present invention provides a method for preparing an article, preferably a medical device, having a modified surface, preferably an elastomeric surface. The method includes providing an article having a surface that includes a polysiloxane and a peroxide, applying a monomer to coat the surface, and heating the coated surface under conditions sufficient to provide the modified surface. Preferably the article is provided with a partially-cured surface. Preferably the partially-cured surface is provided by processing a surface that includes a peroxide curable polysiloxane and a peroxide under conditions sufficient to form the partially-cured surface. Preferably the monomer is applied as an aqueous composition that may optionally include a transition metal salt. Preferably the monomer is water soluble.

In another aspect, the present invention provides a method for preparing a biocompatible medical device. The method includes providing a medical device having a surface that includes a polysiloxane and a peroxide, applying a monomer to coat the surface, heating the surface under conditions sufficient to provide the modified surface, and contacting the surface with a biologically active agent under conditions sufficient to immobilize the biologically active agent on the surface.

In another aspect, the present invention provides a method for preparing a biocompatible medical device. The method includes providing a medical device having a surface that includes a polysiloxane and a peroxide, applying an amide-functional monomer to coat the surface, heating the coated surface under conditions sufficient to provide an amide-functional surface, treating the amide-functional surface under conditions sufficient to convert at least a portion of the amide-functional surface to an amine-functional surface, and contacting the surface with a biologically active agent under conditions sufficient to immobilize the biologically active agent on the surface.

Silicones are commonly prepared by curing (e.g., crosslinking) reactive silicone polymers with conventional free-radical generating cure initiators. For example, vinyl-functional polydimethylsiloxanes (VMQ type silicones) may be blended with peroxides to produce silicone compositions. Silicone compositions may then be molded, extruded, or calendered to produce appropriately shaped articles (e.g., sheets, tubes, gaskets, o-rings, etc.), followed by heating to produce cured articles. Preferably the cured articles are elastomeric. Various types and amounts of reinforcing fillers may be added to silicone compositions to produce elastomers with the desired hardness, modulus, tensile strength, and elongation properties. Silicones are commercially available (e.g., Dow Corning Corp. (Midland, Mich.) and General Electric Co. (Schenectady, N.Y.)) as silicone compositions that include fillers for ease in processing and handling.

Vinyl-functional silicones are commonly used as reactive silicones in the preparation of silicone elastomers. A preferred polymer is poly(dimethylsiloxane-co-methylvinylsiloxane). Suitable commercially available products include those available under the trade designation SILASTIC (e.g., 370, 372, and 373) from Dow Corning (Midland, Mich.).

Preferred organic peroxides are those which are stable at temperatures below about 50° C. and which decompose at a reasonable rate below about 200° C. Suitable peroxides include, for example, benzoyl peroxide, bis(2,4-dichlorobenzoyl) peroxide, dicumyl peroxide, 2,5-dimethyl-2,5-di(t-butylperoxy)hexane, t-butylhydroperoxide, di-t-butyl peroxide, t-butylperoxy benzoate, 2,5-dimethyl-2,5-di(t-butylperoxy)hexyne-3, and lauroyl peroxide. Particularly useful commercially available peroxides are 2,5-dimethyl-2,5-di(t-butylperoxy)hexane, dicumyl peroxide, benzoyl peroxide, and bis(2,4-dichlorobenzoyl) peroxide which are active ingredients of products sold under the trade designations VAROX (from R. T. Vanderbilt Co. Inc., Norwalk, Conn.), DICUP R (from Hercules Inc., Wilmington, Del.), and CADOX BSD and TS50 (from Noury Chemical Corp., Burt, N.Y.). The amount of peroxide used preferably will be at least about 0.1% by weight and more preferably at least about 0.4% by weight based on the weight of silicone polymer. The amount of peroxide used preferably will be at most about 1.0% by weight and more preferably at most about 0.6% by weight based on the weight of silicone polymer.

Finely divided silica may be added as a reinforcing filler to the composition to obtain optimum physical properties (e.g., tensile strength and elongation) of the cured article. If reinforcing filler is used, it is preferably used in about 10 parts by weight to about 50 parts by weight based on the weight of the silicone polymer. Suitable silica reinforcing fillers can be the same as those recommended by manufacturers of silicones as fillers. These include, for example, fumed silica, precipitated silica, carbon black, diatomaceous earth, and combinations thereof. Besides reinforcing fillers, other fillers including extending fillers may also be used. Extending fillers may be incorporated to alter the rheological properties of the composition and may not substantially change the physical properties of the cured article. Such extending fillers include, for example, ground quartz and pigments.

Other additives may optionally be included in the silicone composition to provide the desired Theological and physical properties. Such additives include, for example, silicone oils, antioxidants, adhesion promoters, release agents, pigments, and flame retardants.

Silicone compositions may be prepared, for example, by blending silicone polymers with peroxides and any optional ingredients (e.g., fillers, etc.) to produce silicone compositions. The blending operation may be carried out with conventional rubber mixing equipment including, but not limited to, two-roll mills and internal mixers. The mixing equipment is preferably cooled to regulate the temperature of the silicone composition.

The silicone composition may be shaped into the desired article by any of the standard processing procedures including, but not limited to, molding and extruding. The temperature and pressure are preferably controlled to enable flow of the composition into the mold or through the die without premature curing of the composition. The temperature of the composition is preferably maintained at a temperature of at least about 100° C. and more preferably at least about 110° C. The temperature of the composition is preferably maintained at a temperature of at most about 150° C. and more preferably at most about 120° C.

After forming the composition to the desired shape, the composition may be heated to provide a cured article. The composition may be heated by any suitable method including, but not limited to, conduction, convection, hot air impingement, steam treatment, IR irradiation, UV irradiation, microwave irradiation, and mechanical shearing. Alternatively, the shaping and curing process may be carried out in the same operation. For example, the composition may be heated as it flows into a mold and the heating continued until curing has occurred. Optionally, the curing may be carried out under pressure.

The degree of cure of the composition under various conditions (e.g., time and temperature) may be determined by the use of commercially available rheometers using test methods as described in American Society for Testing and Materials (ASTM) D2084-95 standard. The relative degree of cure of the composition under various conditions may also be determined by solubility and/or swelling measurements, with lower weight gain and/or lower volume swell being indicative of higher degree of cure.

A partially-cured material may have less developed mechanical properties than a fully-cured material. For example, an elastomer is preferably first cured by molding or extruding, and then thermally treated in a post-cure step after removal from the mold or extrusion die. A partially-cured elastomer is preferably obtained before the post-cure step. The amount of cure developed during the molding or extruding step is reflected by standard rheometer curves. For example, data provided by an oscillating disk rheometer (a continuous measurement of the change in torque vs. curing time) may be used to determine the amount of cure that occurred in the mold or extrusion die. The percentage of the maximum torque observed for a partially-cured elastomer compared to the maximum torque observed for a fully-cured elastomer is a measure of the amount of cure.

By specifying the composition formulation (e.g., level and type of peroxide) and regulating the curing conditions (e.g., time, temperature, and pressure), partially-cured samples may be obtained. Preferably a partially-cured elastomer, as measured by an oscillating disk cure meter as described in the ASTM D2084-95 standard, has a maximum observed torque of at least about 20%, more preferably at least about 50%, and most preferably at least about 70% of the maximum torque observed for a fully-cured elastomer. Preferably a partially-cured elastomer has a maximum observed torque of at most about 100% and more preferably at most about 99% of the maximum torque observed for a fully-cured elastomer. Although an elastomer may have about 100% of the maximum torque observed for a fully-cured elastomer, it may still be partially cured for the purpose of this application if it has not been post-cured. Elastomers that have not been post-cured preferably retain substantial amounts of peroxide that have not decomposed.

An aqueous composition may be applied to the partially-cured silicone composition to provide a surface-modified article. Preferably, the aqueous composition includes at least about 1% by weight and more preferably at least about 10% by weight monomer. Preferably, the aqueous composition includes at most about 50% by weight and more preferably at most about 40% by weight monomer. Preferably the monomer is suspendable, dispersable, or soluble in water. Most preferably the monomer is water soluble. The aqueous composition may optionally include a regulator, a material that may regulate the rate of the reaction by altering the rate of free-radical generation. Examples of regulators include, but are not limited to, transition metal salts, for example, iron sulfate, cobalt nitrate, nickel nitrate, copper nitrate, and ruthenium chloride. The level of the regulator, if used, will depend on the amount of surface-modification desired and other conditions, but will preferably be less than about 1.0M, more preferably less than about 0.5M, and most preferably less than about 0.1M.

The monomers that are used in the composition are preferably polymerizable in the presence of free-radicals. Preferred classes of monomers include acrylates and methacrylates. Preferred monomers include, but are not limited, to acrylamide, acrylic acid, methacrylic acid, poly(ethylene glycol)acrylamide, poly(ethylene glycol)methacrylamide, aminoethylmethacrylate, poly(ethylene glycol) methyl ether methacrylate, poly(ethylene glycol) ethyl ether methacrylate, and combinations thereof.

The composition may be applied to the partially-cured silicone composition by any appropriate method including, but not limited to, spray-coating, dip-coating, immersion-coating, and combinations thereof. Preferably the composition is applied by spray-coating or immersion-coating.

After the composition is applied to the partially-cured silicone composition, heat is applied to provide the surface-modified article. The reaction is preferably carried out at a temperature of at least about 80° C. and more preferably at a temperature of at least about 90° C. The reaction is preferably carried out at a temperature of at most about 100° C. The reaction is preferably carried out for at least about 10 seconds and more preferably for at least about 10 minutes. The reaction is preferably carried out for at most about 2 days and more preferably for at most about 2 hours. The reaction may be carried out at atmospheric pressure or at elevated pressure.

The surface-modified articles of the present invention are useful for immobilizing biologically active agents. For example, when acrylamide is used as the monomer in the composition, an amide-functional surface is obtained. The amide functional surface may be converted to an amine-functional surface by the Hoffman degradation process as described in copending U.S. patent application Ser. No. 09/245,834 filed Feb. 8, 1999 entitled "METHOD FOR ATTACHMENT OF BIOMOLECULES TO SURFACES THROUGH AMINE-FUNCTIONAL GROUPS." Biologically active agents (e.g., periodate heparin) may be readily coupled to the amine-functional surface using methods similar to those described in U.S. Pat. No. 5,607,475.

Biologically active agents (e.g., heparin, albumin, phosphorylcholine, dexamethazone, fibrinokinase, collagen, and combinations thereof) may be attached in an appropriate amount and orientation effective to provide an improved nonthrombogenic surface relative to the substrate without the biologically active agent. The methods of the present invention provide relatively high biologically active agent loading capacities (often as high as 50 micrograms of biologically active agents per square centimeter of modified surface) and bioactivities (often as high as 1.0 International Unit (IU) thrombin (IIa) deactivated per square centimeter of modified surface). For example, an article having a modified silicone surface can be surface modified with heparin at a level of up to about 10 micrograms/square centimeter, and can demonstrate a bioactivity of up to about 1.0 IU IIa deactivated per square centimeter.

Medical devices in which the biocompatible material of the present invention can be incorporated include, but are not limited to, surgical implants, prostheses, and any artificial part or device which replaces or augments a part of a living body or comes into contact with bodily fluids, particularly blood. The substrates can be in any shape or form including tubular, sheet, rod and articles of proper shape. Various medical devices and equipment usable in accordance with the invention are known in the art. Examples of devices include catheters, suture material, tubing, and fiber membranes. Examples of catheters include central venous catheters, thoracic drain catheters, and angioplasty balloon catheters. Examples of tubing include tubing used in extracorporeal circuitry, such as whole blood oxygenators. Examples of membranes include hemodialysis membranes, and membranes used in diagnostic or biosensor devices. Also included are devices used in diagnosis, as well as suture material.

Further illustrations of medical devices include the following: autotransfusion devices, blood filters, blood pumps, blood temperature monitors, bone growth stimulators, breathing circuit connectors, bulldog clamps, cannulas, grafts, implantable pumps, impotence and incontinence implants, intra-ocular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

The present invention is illustrated by the following examples. It is to be understood that the particular examples, materials, amounts, and procedures are to be interpreted broadly in accordance with the scope and spirit of the invention as set forth herein.

EXAMPLES

A poly(dimethylsiloxane-co-methylvinylsiloxane) elastomer base containing 2,4-dichlorobenzoyl peroxide catalyst and available under the trade designation MED-4516 was obtained from NuSil (Carpinteria, Calif.). Acrylamide (99.9% purity, triple crystallized) was obtained from Aldrich Chemicals Inc. (Milwaukee, Wis.). Copper(II) nitrate hydrate ($Cu(NO_3)_2 \cdot xH_2O$) (99.999% purity) was obtained from Aldrich Chemicals Inc. (Milwaukee, Wis.). Deionized water was used for all reactions.

Example 1

A silicone elastomer sheet (2 mm thick) was molded from a silicone elastomer base containing the following ingredients: polysiloxane, titanium dioxide (2% by weight), fumed silica (about 30% by weight), and 2,4-dichlorobenzoylperoxide (0.55% by weight). The sheets were precured by molding at 115° C. (atmospheric pressure) for times of 3 minutes, 4 minutes, or 5 minutes. The partially-cured elastomers were immediately placed in reactors containing aqueous compositions of acrylamide (10%, 20%, or 30% by weight). The reactions were carried out at either 80° C., 90° C., or 100° C. for one hour. The reactions carried out at 100° C. were run either in the presence of (0.1 M) or absence of copper(II) nitrate. Relative surface-modification yields were determined by attenuated total reflectance fourier transform infrared spectroscopy (ATR-FTIR). Measurable surface-modification yields reported in Table 1 correspond to the ratio of the ATR-FTIR signals measured at two peaks (1570 cm$^{-1}$ and 780 cm$^{-1}$ ($I_{1570}/I_{780}$)). For pure silicone, the ratio is equal to zero.

TABLE 1

Variation in Surface-Modification Yields by Conditions

| Sample | Acrylamide conc. (wt. %) | Temp. (° C.) | Precuring Time, minutes | $Cu(NO_3)_2$ | Relative Yield |
|---|---|---|---|---|---|
| 1A | 30 | 100 | 3 | No | 0.77 |
| 1B | 30 | 100 | 4 | No | 0.54 |
| 1C | 30 | 100 | 5 | No | 0.31 |
| 1D | 20 | 100 | 3 | No | 0.22 |
| 1E | 30 | 100 | 3 | Yes | 0.04 |
| 1F | 30 | 100 | 4 | Yes | 0.03 |

A polyacrylamide surface-modified sample was modified by the Hoffman degradation process as described in copending U.S. patent application Ser. No. 091245,834 filed Feb. 8, 1999 entitled "METHOD FOR ATTACHMENT OF BIO-MOLECULES TO SURFACES THROUGH AMINE-FUNCTIONAL GROUPS." A calorimetric assay using 2,4, 6-trinitrobenzenesulfonic acid as described in U.S. Pat. No. 6,117,979 (Hendriks et al.) showed the clear presence of primary amines after the degradation reaction. Periodate heparin was successfully coupled to an amine-functional surface-modified silicone elastomer using methods similar to those described in U.S. Pat. No. 5,607,475.

Example 2

Silicone tubing (9 millimeter diameter, about 1 millimeter wall thickness) was extruded under standard conditions with no post-cure using silicone composition similar to that described in Example 1.

Surface-modification of the partially-cured elastomer was carried out three days after the tubing was extruded. Aqueous compositions of acrylamide (40% by weight) and copper (II) nitrate (from 0.005M to 0.1M) were prepared. Surface-modification using an immersion technique at atmospheric pressure was carried out at 100° C. for 90 minutes. High polyacrylamide surface-modification yield was obtained on all samples. The surface-modification yield decreased with increasing copper(II) nitrate concentration.

The complete disclosure of all patents, patent applications, and publications, and electronically available material cited herein are incorporated by reference.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to biocompatible devices. The present invention is also not limited to medical devices per se, but may find further applications such as, for example, coated cosmetic articles. The present invention further includes within its scope methods of making and using the articles described hereinabove.

What is claimed is:

1. A method for preparing an article having a modified surface, the method comprising:
   providing an article having a surface that is partially cured, the surface comprising a polysiloxane and a peroxide;
   applying a monomer to coat the surface; and
   heating the coated surface under conditions sufficient to provide the modified surface with an attached polymer.

2. The method of claim 1 wherein providing an article having a surface that is partially cured comprises:
   providing a surface comprising a peroxide curable polysiloxane and a peroxide; and
   processing the surface under conditions sufficient to form a partially-cured surface using a method selected from the group consisting of extruding, molding, and heating.

3. The method of claim 2 wherein the peroxide curable polysiloxane comprises poly(dimethylsiloxane-co-methylvinylsiloxane).

4. The method of claim 2 wherein processing the surface comprises heating the surface by a method selected from the group consisting of conduction, convection, hot air impingement, steam treatment, infrared irradiation, ultraviolet irradiation, microwave irradiation, mechanical shearing, and combinations thereof.

5. A method for preparing a biocompatible medical device comprising:
   providing a medical device having a surface that is elastomeric, the surface comprising a polysiloxane and a peroxide;
   applying a monomer to coat the surface;
   heating the surface under conditions sufficient to provide the modified surface with an attached polymer; and
   contacting the surface wit a biologically active agent under conditions sufficient to immobilize the biologically active agent on the surface, wherein the biologically active agent is selected from the group consisting of heparin, albumin, phosphorylcholine, dexamethazone, fibrinokinase, collagen, and combinations thereof.

6. A method for preparing a biocompatible medical device comprising:
   providing a medical device having a surface, the surface comprising a polysiloxane and peroxide;
   applying an amide-functional monomer to coat the surface;
   heating the coated surface under conditions sufficient to provide an amide-functional surface;
   treating the amide-functional surface under conditions sufficient to convert at least a portion of the amide-functional surface to an amine-functional surface; and
   contacting the surface with a biologically active agent under conditions sufficient to immobilize the biologically active agent on the surface.

7. The method of claim 6 wherein the biologically active agent is selected from the group consisting of heparin, albumin, phosphorylcholine, dexamethazone, fibrinokinase, collagen, and combinations thereof.

* * * * *